(12) United States Patent
Barnes et al.

(10) Patent No.: US 6,849,151 B2
(45) Date of Patent: Feb. 1, 2005

(54) MONITORING SUBSTRATE PROCESSING BY DETECTING REFLECTIVELY DIFFRACTED LIGHT

(76) Inventors: Michael S. Barnes, 12215 Santa Teresa Dr., San Ramon, CA (US) 94583; John P. Holland, 1565 Calaveras Ave., San Jose, CA (US) 95126; David S. L. Mui, 48472 Arkansas Pl., Fremont, CA (US) 94539; Wei Liu, 5035 Moorpark Dr., San Jose, CA (US) 95129

( * ) Notice: Subject to any disclaimer, the term of this patent is extended or adjusted under 35 U.S.C. 154(b) by 45 days.

(21) Appl. No.: 10/215,065

(22) Filed: Aug. 7, 2002

(65) Prior Publication Data

US 2004/0026368 A1 Feb. 12, 2004

(51) Int. Cl.[7] ............ H05H 1/00; C23C 16/00; H01L 21/00
(52) U.S. Cl. ............ 156/345.24; 118/712; 438/7
(58) Field of Search ............ 156/345.24, 345.25; 118/712; 438/7, 8, 9, 14, 16; 427/8, 569

(56) References Cited

U.S. PATENT DOCUMENTS

| | | | |
|---|---|---|---|
| 4,454,001 A | 6/1984 | Sternheim et al. | |
| 4,772,128 A | * 9/1988 | Vinarub et al. | 356/635 |
| 5,337,144 A | 8/1994 | Strul et al. | |
| 5,450,205 A | 9/1995 | Sawin | |
| 5,578,161 A | * 11/1996 | Auda | 438/9 |
| 6,052,188 A | 4/2000 | Fluckiger et al. | |
| 6,081,334 A | 6/2000 | Grimbergen et al. | |
| 6,090,302 A | 7/2000 | Smith | |
| 6,160,621 A | 12/2000 | Perry et al. | |
| 6,521,080 B2 | 2/2003 | Balasubramhanya | |
| 6,537,833 B1 | * 3/2003 | Lensing | 438/14 |
| 2002/0001862 A1 | 1/2002 | Ushio | |
| 2003/0052084 A1 | * 3/2003 | Tabery et al. | 216/59 |

* cited by examiner

*Primary Examiner*—Parviz Hassanzadeh
(74) *Attorney, Agent, or Firm*—Janah & Associates; Joseph Bach (57) ABSTRACT

A substrate is placed in a process zone and an energized process gas is maintained in the process zone to process the substrate. A light beam is reflectively diffracted from a pattern of features of the substrate being processed, the reflected beam is monitored, and a signal is generated in relation to the monitored beam. During processing, a width of the features of the substrate can change. The generated signal is evaluated to detect the occurrence of a change in the width of the features.

9 Claims, 7 Drawing Sheets

MONITORING SUBSTRATE PROCESSING BY DETECTING REFLECTIVELY DIFFRACTED LIGHT

BACKGROUND

The present invention relates to monitoring the processing of a substrate by reflecting light from features being processed on the substrate.

In the processing of substrates to fabricate electronic circuits and displays, semiconductor, dielectric, and conductor materials, are formed on a substrate by chemical vapor deposition (CVD), physical vapor deposition (PVD), oxidation, nitridation, ion implantation, and etching processes. In CVD processes, a reactive gas is used to deposit material on the substrate. In PVD processes, a target is sputtered to deposit material on the substrate. In oxidation and nitridation processes, an oxide or nitride material, such as silicon dioxide or silicon nitride, is formed on the substrate by exposing the substrate to a suitable gaseous environment. In ion implantation, ions are implanted into the substrate. In subsequent etching processes, etch-resistant features comprising resist or hard-mask, are formed on the substrate and the exposed portions of the substrate between the etch-resistant features (substrate open area) are etched to form patterns of gates, vias, contact holes or interconnect lines.

During such processing, a process monitoring method may be used to evaluate and control the process, for example, to stop or change the process at a process endpoint. In interferometric monitoring methods, interference peaks that result from the constructive and destructive interference of a radiation that is reflected from the substrate, over time, are counted to determine an etching depth into the substrate or a thickness of material deposited on the substrate. For example, in etching processes, as exposed portions of the substrate between etch-resistant features are etched to increasing depths, the intensity of the radiation reflected from the portions being etched and from underlying or adjacent material, modulates to form constructive and destructive interference peaks. By counting the interference peaks, the depth of the etched portions and the etching rate may be evaluated.

However, while such process monitoring methods can be used to determine vertical etching rates and etching depths, they are often not effective in evaluating other changing attributes of features being formed in the substrate. For example, conventional interferometric methods cannot be used to accurately determine changes in widths or other dimensions of the features being formed on the substrate, which are sometimes the critical dimensions. A change in a width of a feature may occur when sidewalls of the feature are being etched away or when material is deposited into the feature. While rate of etching of the feature depth is sometimes used to estimate the rate of etching of the sidewalls of the features, the two etching rates are often quite different, especially in processes in which the etching species have a kinetic energy component that enhances etch rates in the vertical direction relative to horizontal sidewall etching rates.

Thus, it is desirable to be able to monitor a changing shape or width of features being processed in a substrate, especially in the etching of features having critical dimensions or shaped profiles.

SUMMARY

In a method of processing a substrate in a process zone, the substrate is placed in a process zone. The substrate comprises a surface with a pattern of features thereon, at least some of the features having a width. An energized process gas is provided in the process zone to process the substrate to change the width of the features. A light beam is directed on the substrate, the light beam comprising multiple wavelengths that are selected so that the light beam is reflectively diffracted by the pattern of features to generate a reflectively diffracted light beam having wavelengths with intensities that modulate in relation to the changing width of the features. It is determined when the features have a desired width by detecting and evaluating the modulated intensities of the multiple wavelengths of the reflectively diffracted light beam.

The method can further include generating a signal trace of the intensities of the reflectively diffracted light beam as a function of their wavelengths and comparing the generated signal trace to a predetermined reference trace having an intensity at a wavelength $\lambda$ (nm) that is approximately proportional to $[\sin(\pi b\phi/\lambda)/(\pi b\phi/\lambda)]^2$, where b (nm) is the width of the features and $\phi$ (radians) is the angle of detection measured from the normal to the surface of the substrate at the place where the light beam is incident.

A substrate processing chamber includes a support to support a substrate comprising a surface with a pattern of features thereon, at least some of the features having a width. A gas supply is also included to provide a process gas in the chamber. A gas energizer energizes the process gas to process the substrate to change the width of the features. A light beam source directs a light beam on the substrate, the light beam comprising multiple wavelengths that are selected so that the light beam is reflectively diffracted by the pattern of features to generate a reflectively diffracted light beam having wavelengths with intensities that modulate in relation to the changing width of the features. A light detector detects the modulated intensities of the multiple wavelengths of the reflectively diffracted light beam. And a controller is provided to determine when the features have a desired width by evaluating the modulated intensities.

The controller can further be adapted to generate a signal trace of the intensities of the reflectively diffracted light beam as a function of their wavelengths and compare the generated signal trace to a predetermined reference trace having an intensity at a wavelength $\lambda$ (nm) that is approximately proportional to $[\sin(\pi b\phi/\lambda)/(\pi b\phi/\lambda)]^2$, where b (nm) is the width of the features or the width of the open areas between the features, and $\phi$ (radians) is the angle of detection measured from the normal to the surface of the substrate at the place where the light beam is incident.

DRAWINGS

These features, aspects, and advantages of the present invention will become better understood with regard to the following description, appended claims, and accompanying drawings which illustrate examples of the invention. However, it is to be understood that each of the features can be used in the invention in general, not merely in the context of the particular drawings, and the invention includes any combination of these features, where:

DESCRIPTION

Figure 1A:
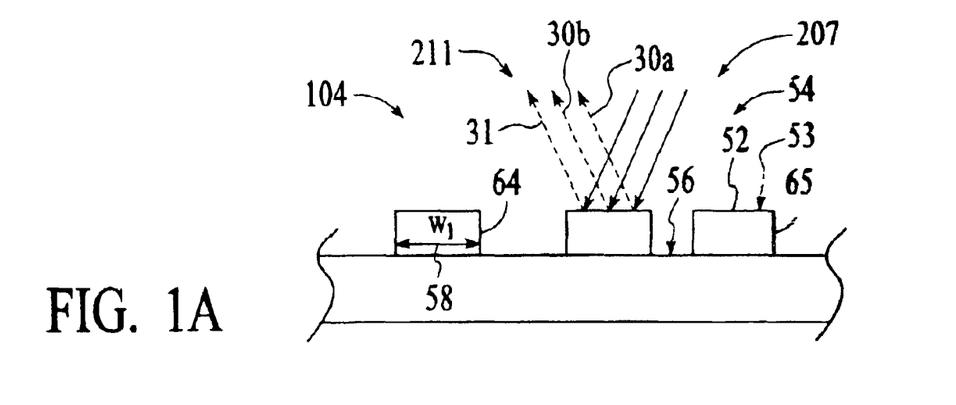
FIGS. 1a through 1c are partial sectional views of a substrate having a pattern of features that are etched to change a width of the features.

A substrate processing stage involves processing a substrate 104 comprising features 52 that form a repetitive and periodic pattern 54 on a surface 56 of the substrate 104, such as shown in FIG. 1a. For example, the substrate 104 may comprise a pattern 54 of projecting features 52 that rise above open areas 56 of the substrate 104. Processing of the substrate 104 may comprise, for example, etching of the features 52 or the open areas 56 between the features 52, or depositing material 59 on or between the features 52. As the process is performed, for example as the substrate 104 is etched or as material 59 is deposited, the geometry of the features 52 may change, thereby changing the overall pattern of the features 52. The change in geometry of the features 52 may comprise intentional or unintentional changes in critical dimensions of the features 52, such as for example a change in a width 58 of the features 52 resulting from etching the sidewalls 64 of the features 52 or from depositing material 59 over the features 52.

Processing of the substrate 104 is monitored by detecting the light beam 211 that is reflectively diffracted by the periodic pattern 54 of features 52 being processed on the substrate 104. The pattern 54 of features 52 acts similarly to a diffraction grating and reflectively diffracts light that is incident on the substrate 104. The reflectively diffracted light beam 211 constructively and destructively interferes with itself to form a diffraction pattern, which is a series of bright and dark fringes that may be detected. For example, as illustrated in FIG. 1a, first and second light beam components 30a,b, 31 are incident on the tops 53 of features 52 and the open areas 56 between the features 52, and at least a portion of the first and second components 30a,b, 31 are reflectively diffracted from the substrate 104. Because the first and second components 30a,b, 31 all have different pathlengths resulting from reflection from different points at the tops 53 of the features 52, these light beam components 30a,b, 31 acquire different phases in their propagation paths, and constructive and destructive interference of the light beam components 30a,b, 31 occurs. The interference between multiple such light beam components diffracted from various regions of the periodic pattern 54 yields the overall diffraction pattern.

Figure 1B:
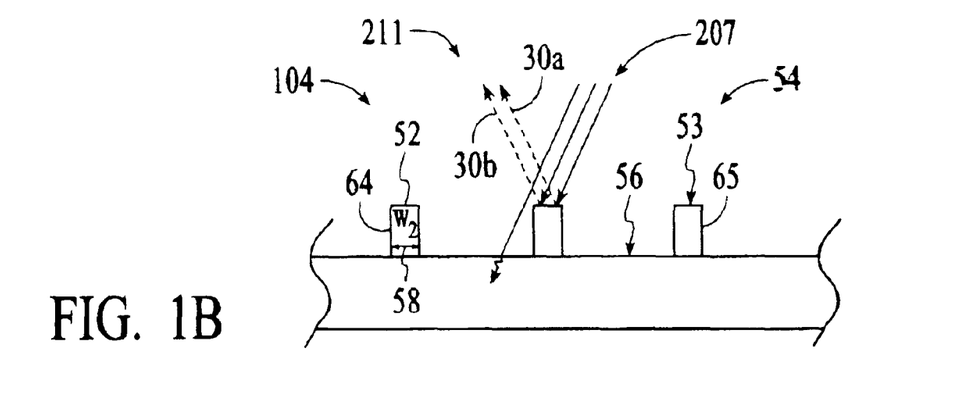

As the substrate 104 is being processed and the periodic pattern 54 of features 52 is changed, as shown in FIG. 1b, the intensities of the bright fringes, or diffraction orders, may be modulated. For example the intensities of the diffraction orders may be modulated as portions of the sidewalls 64 of the features 52 are etched or as material 59 is deposited on the sidewalls 64 of the features 52. In an example of one version (as shown), for the purposes of explanation, the modulation in the intensities is due to an elimination of the second component 31 of the light beam because the portion of the top 53 of the feature 52 from which the second component 31 was reflected has been etched away as the substrate 104 was processed, resulting in an overall change in the constructive and destructive interference of the reflectively diffracted light beam 211. For example, as the sidewalls 64 of the features 52 are etched, the features 52 are etched back to a smaller width and the second component 31 becomes incident on the open areas 56 between the features 52 and absorbed or diffracted with a different path length. The diffraction pattern formed from the constructive and destructive interference of the first and second components 30a,b, 31 is modulated into constructive and destructive interference between only the first components 30a,b. Thus, by changing the periodic pattern 54 of features 52, for example by changing the width of the features 52, the intensities of the diffraction orders are modulated over time, and one or more of these diffraction orders may be detected to monitor the changing shape of the features 52 being processed on the substrate 104.

Alternatively, in another version (not shown), the light beam 207 is reflected from the open areas 56 and absorbed in the features 52. As etching progresses in this version, the open area 56 is increased and more light (rather than less light as in the previous version) is reflected from the substrate 104. As the width of the features 52 decreases, less light impinges on the features 52 and is absorbed.

The multiple wavelengths of the light beam 207 are selected so that the light beam 207 is reflectively diffracted by the pattern of features 52 to generate a diffracted light beam comprising multiple wavelengths having intensities that modulate in relation to the changing width 58 of the features 52. The incident light beam 207 comprising the multiple wavelengths is at least partially diffracted by the periodic pattern 54 of features 52 on the substrate 104 and the intensities of each wavelength of the diffracted light beam are each differently modulated by the changing periodic pattern 54 of features 52. The degree of modulation of the different wavelengths of light beam depends upon the degree of absorption and diffraction of each light beam wavelength by the periodic pattern 54. Thus, the detected intensities of the diffracted multiple wavelengths of the light beam provide information about the stage of the process being performed on the substrate 104.

The diffraction of the light beam 207 from the features 52 of the substrate 104 is a combination of Fraunhofer diffraction involving mutual interference of light from different points on the surface of each feature 52, or alternatively from different points of the open area 56, and another diffraction factor involving mutual interference from the multiple features 52. However, because the width of the features 52 is changing and the center-to-center distance is substantially fixed, the change in the signal trace is due primarily to the Fraunhofer diffraction, such that the intensity to wavelength $\lambda$ (nm) function's signal trace corresponds to:

$$\left(\frac{\sin(\pi b\phi/\lambda)}{\pi b\phi/\lambda}\right)^2 \quad (1)$$

where b (nm) is either the width of the features 52 (if reflection is occurring from the features 52) or the width of the open areas 56 between the features 52 (if reflection is occurring from the open areas 56 between the features 52), and φ (radians) is the angle of detection measured from the normal to the surface 56 of the substrate 104 at the place where the light beam 207 is incident. Typically, the intensity to wavelength function is approximately proportional to the mathematical expression (1). From this known relationship, the wavelength (λ) can be selected to produce a measurable change in intensity for the desired change in feature or open area width (b). The wavelength (λ) can be further selected to maximize the change in intensity for the desired change in feature or open area width (b). In one embodiment, the light beam 207 has wavelengths such that the ratio of the wavelength to the feature width is from about 1.2:1 to about 11:1.

Figure 2:
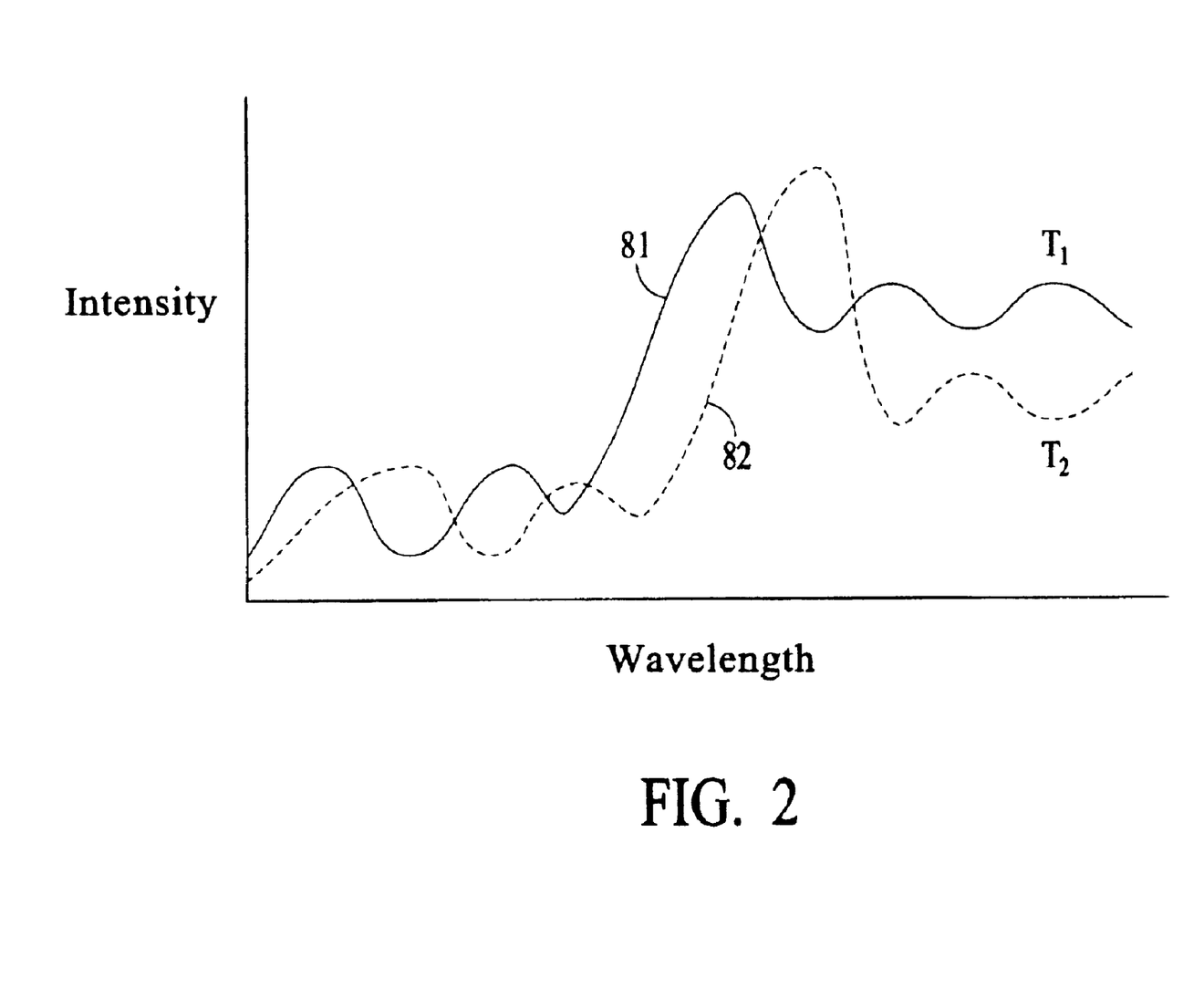
FIG. 2 is a graph of signal traces of the intensity of light that is reflectively diffracted from a pattern of features on a substrate as a function of the wavelength of the incident light beam.

Upon detection of the reflectively diffracted light beam 211, one or more signals are generated in relation to the detected light beam 211. The signal may be evaluated by, for example, processing the signal to evaluate the intensity of the signal for any given wavelength of light. In one version, the signal is evaluated to provide a signal trace of the intensities of a plurality of wavelengths of diffracted light beam as a function of the wavelength, as for example, shown by lines 81 and 82 in FIG. 2. As processing of the substrate 104 progresses, the shape of the signal trace changes due to modulation of the diffracted light beam by the changing pattern 54, thereby allowing for monitoring of the process. For example, the signal trace may evolve during processing from the trace line 81 at an early stage at a time T1 during the substrate process to the trace line 82 that occurs at a later stage at a time T2. The signal traces can be generated at selected intervals or even continuously during processing of the substrate 104, thereby showing the evolution of the diffracted signal during the process.

In one version, the endpoint of a substrate processing stage may be determined by evaluating the signal trace to identify a characteristic attribute of the signal trace. The characteristic attribute may be a relative intensity of one or more wavelengths, such as for example a valley, peak or slope in the signal trace that is indicative of the endpoint of the substrate processing stage. In one version, the signal trace may be evaluated to identify a characteristic attribute that occurs when a predetermined feature shape or geometry is achieved. For example, when the features 52 are etched to a predefined desired width 58, or when a desired thickness of material 59 is deposited on the features 52 (as shown in FIG. 4b), the signal trace may be evaluated to determine when the predefined width of the features 52 is achieved.

The characteristic attribute may be identified by comparing the signal trace to a predetermined reference trace, such as for example a reference trace generated at known endpoint of a substrate processing stage. The signal trace may be compared to the reference trace to determine whether a characteristic attribute of the reference trace, such as a peak, valley or slope of the reference trace, is present in the signal trace, and thus whether the endpoint of the substrate processing stage has been reached. The signal trace may be compared to the reference trace using a computational technique, such as for example by programming windows to check the slopes of the signal trace and compare them to the reference trace, by using a neural network, or some other set of predetermined criteria, to determine if the characteristic attributes of the signal trace are present.

Figure 3A:
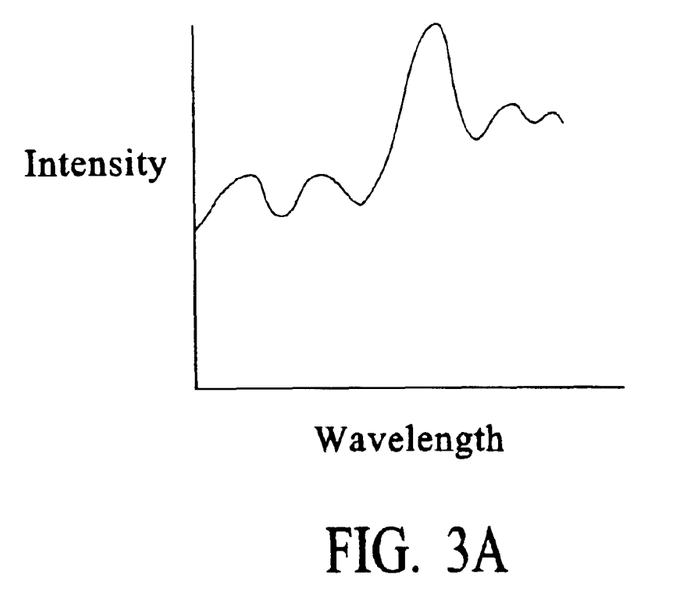
FIG. 3a is a graph of a signal trace of the intensity of light that is reflectively diffracted from a pattern of features on a substrate as a function of wavelength for light polarized in a transverse direction with respect to a principle orientation of the features.
Figure 3B:
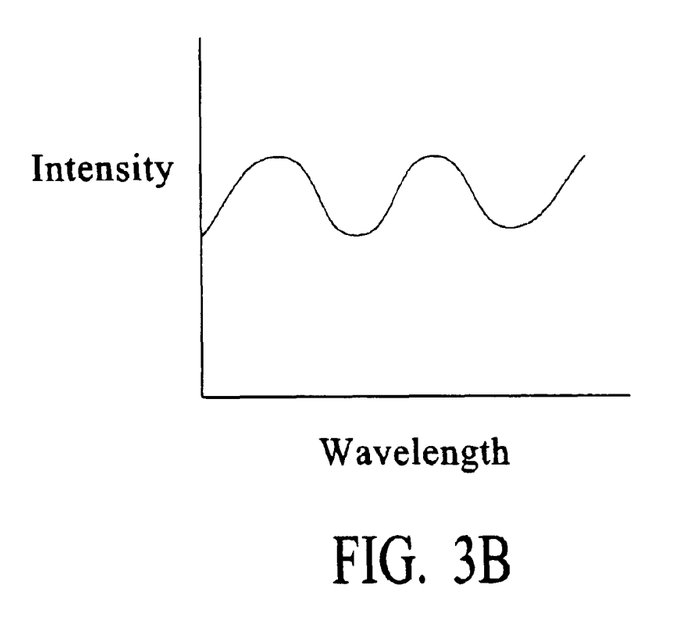
FIG. 3b is a graph of a signal trace of the intensity of light that is reflectively diffracted from a pattern of features on a substrate as a function of wavelength for light polarized in a parallel direction with respect to a principle orientation of features on a substrate.

In one version, the light beam 207 directed to be incident on the substrate 104 or the light beam 211 reflectively diffracted from the substrate 104, is polarized at one or more polarization angles. In one version, the light beam is polarized to one or more polarization angles that are selected according to a principal orientation of features 52 on the substrate 104. The principle orientation may be an orientation along which a majority of features 54 are directed. For example, electrically connecting interconnect lines are oriented along principal orientation directions to minimize cross-over signals. The polarization angles may be selected to align the light beam with respect to one or more axes of such principle orientations. Light polarized at one or more such polarization angles are differently diffracted by the periodic pattern of features 52. For example, FIGS. 3a and 3b show traces of the diffracted light intensity for a plurality of wavelengths that are polarized in a transverse direction (FIG. 3a) and parallel direction (FIG. 3b) with respect to a principle orientation of the features 52. Comparison of the figures shows that the shape of the signal trace changes with the polarization angle of the light beam. Thus, polarizing the light beam to one or more polarization angles provides more information about the substrate process. Furthermore, the polarized light beam may allow for better determination of characteristic attributes of the detected intensity trace. For example, characteristics attributes of the intensity trace that might otherwise be obscured with unpolarized light may be revealed by polarizing the light beam to desired polarization angles, such as for example a single polarization angle that is selected according to a principle orientation of the features 52 of the pattern 54.

The present method and apparatus for monitoring diffracted light provides substantial improvements over conventional processes in determining the endpoint of substrate processing stages, for example in detecting an endpoint of a substrate processing stage that occurs for a predetermined width 58 of the features 52 being processed on the substrate 104. For example, the present method can monitor a process that changes the width 58 of features 52, such as when portion of the sidewalls 64 of the features 52 are being etched, or when the width 58 of the features 52 are being increased, for example when a layer of material 59 is being deposited over the substrate 104 and features 52. The endpoint of these processes may be difficult to determine using conventional techniques, because many of these techniques depend on detecting a change in the depth of an open area between the features 52. With the present invention, the diffraction pattern resulting from directing incident light onto the periodic pattern 54 of features 52 may be dependent on the width 58 of the features 52 or the width of the open areas 56 between the features 52, and thus the detected diffraction orders are modulated according to any changes that occurs to the feature width 58. Thus, this method allows for determination of the endpoint based on the change in the width 58 of the features 52, and is not limited to processes in which the depth of open areas between the features 52 is being changed.

Figure 4A:
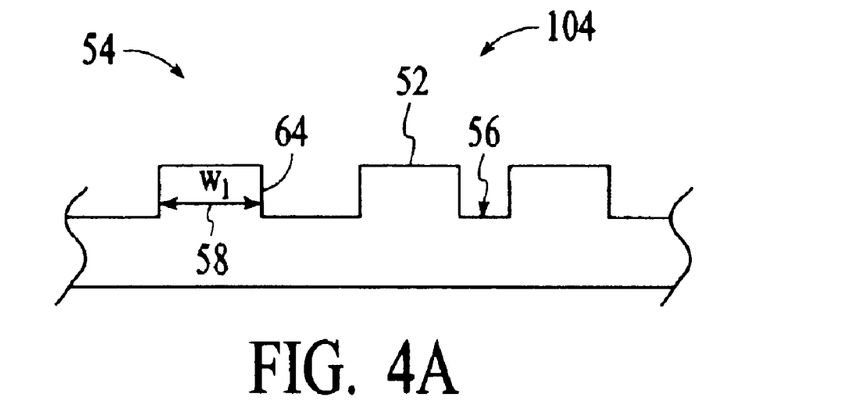
FIGS. 4a and 4b are partial sectional views of features on a substrate at different stages in a deposition process that changes the width of the features.
Figure 4B:
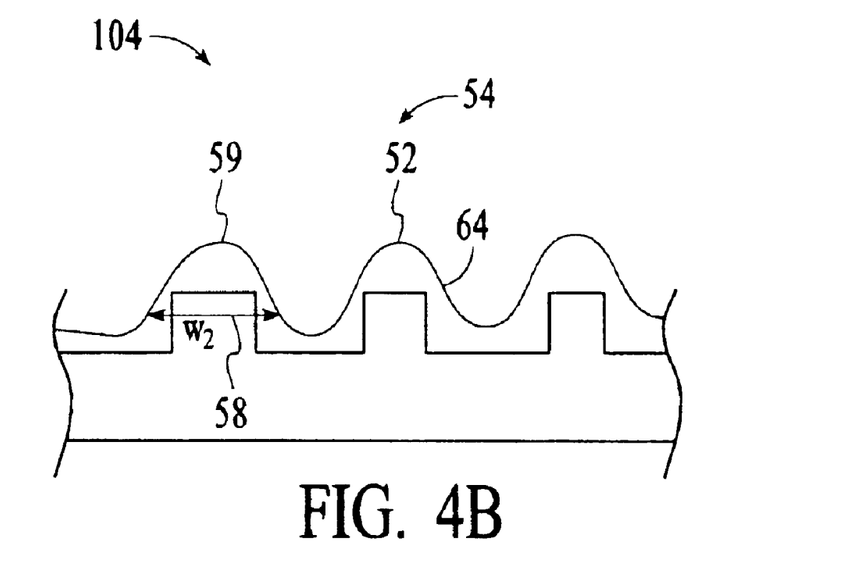
Figure 5A:
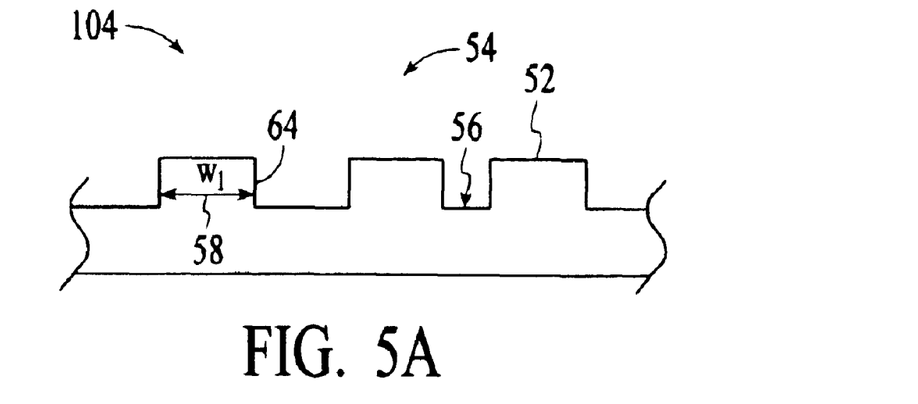
FIGS. 5a and 5b are partial sectional views of features on a substrates at different stages in an feature shaping etching process.
Figure 5B:
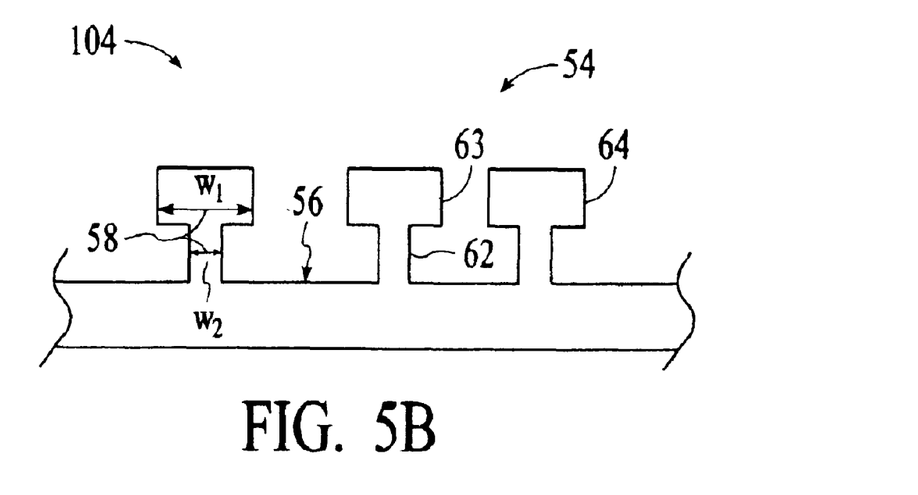

FIGS. 1a and 1b, and 4a through 5b demonstrate examples of processes that may be monitored and that involve a change in the width 58 of the features 52. For example, FIGS. 1a and 1b demonstrate a process in which the width 58 of features 52 on the substrate is being decreased, for example, by etching the features 52, from a width 58 of w1 shown in FIG. 1a to a width 58 of w2, shown in FIG. 1b, where w2<w1. With the change in the width 58 of the features 52, the periodic pattern 54 of features on the substrate 104 changes and the signal trace of the reflectively diffracted light beam 211 is modulated, for example, from the signal trace line 81 to the signal trace line 82 in FIG. 2. Thus, the signal trace may be evaluated to identify characteristic attributes indicative of a processing endpoint that is reached upon attaining the desired predetermined feature width 58 w2. FIGS. 4a and 4b demonstrate another process in which a material 59 is deposited over the substrate 102 and results in an increase in the width 58 of the features 52 from w1 shown in FIG. 4a to w2 shown in FIG. 4b, where w2>w1. Because the width 58 of the features 58 increases during the process, the signal trace will be accordingly modulated during processing and may be evaluated to identify characteristic attributes which indicate that a desired thickness of the deposition material 59 on the sidewalls 64 of the features 52, and thus the desired predetermined width w2 of the features 52, is achieved. FIGS. 5a and 5b demonstrate yet another process in which the lower portions 62 of sidewalls 64 of the features 52 are etched from the width w1, shown in FIG. 5a to a smaller width w2, shown in FIG. 5b. An upper portion 63 of the features remains substantially un-etched at a larger width 58, such as for example a width of about w1. The changing width 58 of the lower portions 62 of the features 52 during processing results in modulation of the signal trace, which may be analyzed to determine when the desired predetermined lower portion width 58 have been attained.

In another version, the process is monitored to ensure that a substantially constant width of the features 52 is maintained. The signal trace is monitored, and a change in the signal trace may be determined to indicate an undesirable change in the feature width. For example, in the vertical etching of vias or contact holes in the substrate 104, it may be desirable to have a substantially constant width of the features 52 throughout the etching step.

The process monitoring method described above may be used in an apparatus 102 suitable for processing a substrate 104. Such an apparatus 102, according to the present invention, comprises a process chamber 106, such as a decoupled plasma source (DPS) chamber, schematically illustrated in FIG. 6, and commercially available from Applied Materials Inc., Santa Clara, Calif. The particular embodiment of the apparatus 102 shown herein is suitable for processing substrates 104, such as semiconductor wafers, and may be adapted by those of ordinary skill to process other substrates 104, such as flat panel displays, polymer panels, or other electrical circuit receiving structures. The apparatus 102 is provided only to illustrate the invention, and should not be used to limit the scope of the invention or its equivalents to the exemplary embodiments provided herein. The apparatus 102 may be attached to a mainframe unit that contains and provides electrical, plumbing, and other support functions for the apparatus 102. Exemplary mainframe units compatible with the illustrative embodiment of the apparatus 102 are currently commercially available as the Centura™ systems from Applied Materials, Inc., of Santa Clara, Calif.

Generally, the apparatus 102 comprises an chamber 106 comprising walls typically fabricated from metal or ceramic materials. In the embodiment shown, the chamber 106 comprises a wall which may comprise sidewalls 114, a bottom wall 116, and a ceiling 118. The ceiling 118 may comprise a substantially arcuate shape, or in other versions, the ceiling 118 may comprise a dome, substantially flat, or multi-radius shaped portion. The chamber 106 typically comprises a volume of at least about 5,000 $cm^3$. In operation, process gas is introduced into the chamber 106 through a gas delivery system 130 that includes a process gas supply 138, conduits 136 having flow control valves 134, and gas outlets 142 around a periphery of the substrate 104 which may be held on a support 110. Alternatively to the configuration shown in FIG. 6, the process gas may be introduced through a showerhead (not shown) mounted on the ceiling 106 of the chamber. Spent process gas and etchant byproducts are exhausted from the chamber 106 through an exhaust system 144 which includes a pumping channel 146 that receives spent process gas, a throttle valve 150 to control the pressure of process gas in the chamber 106, and one or more exhaust pumps 152. The exhaust system 144 may also contain a system for abating undesirable gases from the exhaust.

Figure 6:
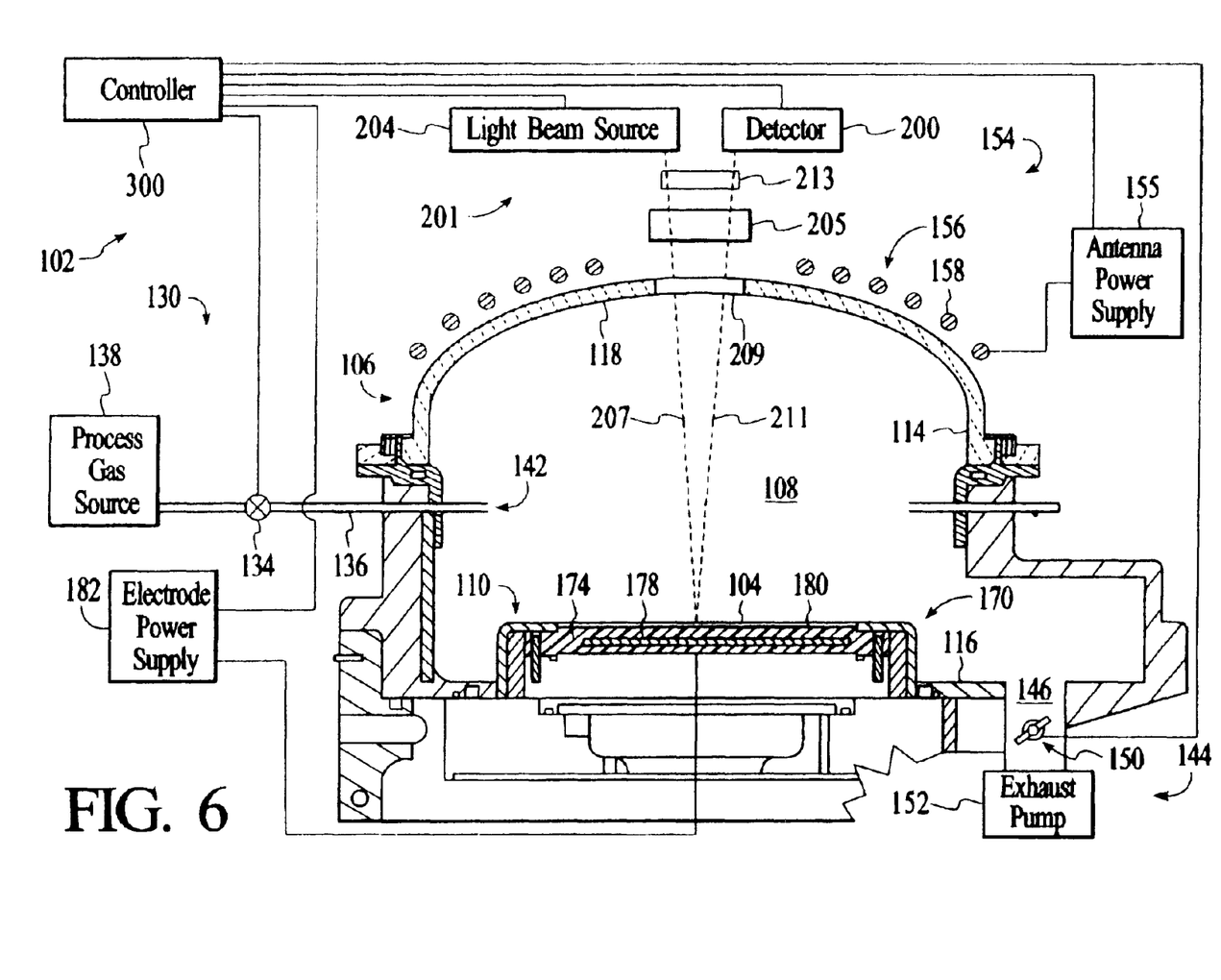
FIG. 6 is a schematic sectional side view of an exemplary embodiment of a substrate processing chamber according to the present invention.

The process gas is energized to process the substrate 104 by a gas energizer 154 that couples energy to the process gas in the process zone 108 of the chamber 106 (as shown) or in a remote zone upstream from the chamber 106 (not shown). In one version, the gas energizer 154 comprises an antenna 156 comprising one or more inductor coils 158 which may have a circular symmetry about the center of the chamber 106. Typically, the antenna 156 comprises solenoids having from about 1 to about 20 turns. A suitable arrangement of solenoids is selected to provide a strong inductive flux linkage and coupling to the process gas. When the antenna 156 is positioned near the ceiling 118 of the chamber 106, the adjacent portion of the ceiling may be made from a dielectric material, such as silicon dioxide, which is transparent to RF or electromagnetic fields. An antenna power supply 155 provides, for example, RF power to the antenna 156 at a frequency of typically about 50 kHz to about 60 MHz, and more typically about 13.56 MHz; and at a power level of from about 100 to about 5000 Watts. An RF match network not shown) may also be provided. Alternatively or additionally, the gas energizer 154 may comprise a microwave or remote gas activator (not shown).

In one version, the gas energizer 154 may also or alternatively comprise process electrodes (not shown) that may be used to energize or further energize the process gas. Typically, the process electrodes include one electrode (not shown) in a wall, such as a sidewall 114 or ceiling 118 of the chamber 106 that may be capacitively coupled to another electrode, such as an electrode in the support 110 below the substrate 104. The electrode may comprise a dielectric ceiling 118 that serves as an induction field transmitting window that provides a low impedance to an RF induction field transmitted by the antenna 156 above the ceiling 118. Suitable dielectric materials that can be employed include materials such as aluminum oxide or silicon dioxide. Generally, the electrodes may be electrically biased relative to one another by an electrode voltage supply (not shown) that includes an AC voltage supply for providing an RF bias voltage. The RF bias voltage may comprise frequencies of about 50 kHz to about 60 MHz, and is preferably about 13.56 MHz, and the power level of the RF bias current is typically from about 50 to about 3000 Watts.

The support 110 may comprise an electrostatic chuck 170 comprising a dielectric body 174 that at least partially covers an electrode 178 and which may include a substrate receiving surface 180. The electrostatic chuck 170 is capable of generating an electrostatic charge for electrostatically holding the substrate 104 to the support 110. The electrode 178 may also be a separate structure, such as a cathode, below an electrostatic chuck. The electrode 178 may also serve as one of the process electrodes discussed above. An electrode power supply 182 provides the voltage to the electrode 178.

The apparatus 102 may further comprise a process monitoring system 201 adapted to monitor a process in the chamber 106, an example of which is shown in FIG. 6. The process monitoring system 201 may comprise a light beam source 204 to provide a light beam 207 comprising multiple wavelengths that is incident on the substrate 104, and a light detector 200 that detects the reflectively diffracted light beam 211 from the substrate 104. A light beam source 204 suitable to generate the plurality of wavelengths may comprise a light beam source 204 that is a broadband light beam source, such as a xenon or deuterium lamp; or the plasma emission light may be reflectively diffracted from the substrate 104 may be filtered using suitable filters to monitor different discrete wavelengths of the light. For example, a light beam source 204 adapted to generate an incident light beam 207 comprising wavelengths of from about 300 nm to about 700 nm, may be reflectively diffracted from features 52 having a width of from about 0.1 to about 1 microns, to provide better endpoint detection. The process monitoring system 201 may further comprise a light polarizer 213 positioned in the path of the incident light beam 207 or reflectively diffracted light beam 211 to polarize the light beam 207, 211.

In one version of a vertical etching process in a conventional method, one or more different layers of material are typically uncovered and exposed to the plasma during etching, causing sudden changes in the chemistry of the plasma and corresponding sudden changes in the emission of light from the plasma. A flash lamp operated to have repetitive "off" periods can be used to determine the plasma emission alone by detecting light during the "off" periods. These sudden changes in plasma emission are detected and their effect is subtracted before determining endpoint. However, flashed lamps are limiting because of decreased operational lifetimes, the production of a large amount of heat, the large power supplies required to drive the flashed lamps, and limited flash repetition rates.

To avoid these limitations in the present method, the light beam source 204 may be a non-pulsed light beam source directing a non-pulsed light beam that is substantially continuously turned on during the endpoint detection process. For example, the light beam may be substantially constant or vary smoothly. In this version, the processing can occur substantially horizontally on the substrate 104 to change the width of the features 52, such that substantially the same material is constantly being processed and sudden chemistry changes do not arise. For example, the process may comprise horizontal etching of the features 52 to decrease the width of the features 52. Thus, the plasma chemistry and the light emitted by the plasma are substantially predetermined, and a non-pulsed light beam source can be used.

A light permeable window 209 may be provided in a wall of the chamber 106 to allow the light beam 207, 211 to pass therethrough. In operation, the light beam 207 from the light beam source 204 may be generated by a plasma emission in the chamber or may be from a separate light beam source 204 that directs the light beam onto the substrate 104. At least a portion of the light beam 207 is reflectively diffracted by the features 52 on the substrate 104. This light beam 211 is detected by the light detector 200, and a signal may be generated by the light detector 200 in relation to the intensity of the reflected light beam 211. The signal is sent to a controller 300 having a signal processor that is capable of analyzing the signal to determine whether, for example, the endpoint of a substrate processing stage has been reached. The light beam source 204 may also comprise a collimator 205, comprising, for example, one or more lenses that are adapted to focus and collimate the diffracted light beam 207 onto the substrate 104 or detector 200. Furthermore, one or more polarizers 213 may be provided in the path of the incident light beam 207 or reflectively diffracted light beam 211 to polarize the light beam to one or more polarization angles.

To process a substrate 104, the process chamber 106 is evacuated and maintained at a predetermined subatmospheric pressure. The substrate 104 is then provided on the support 110 by a substrate transport 101, such as for example, a robot arm and a lift pin system. The gas energizer 154 couples RF or microwave energy to the process gas to provide an energized gas in the process zone 108. The energized gas processes the substrate 104, for example, by etching features 52 on the substrate 104 or by depositing a material 59 on the substrate 104. Processing of the substrate 104 is monitored by the process monitoring system 201. Spent process gas and process by-products are exhausted by the exhaust 144.

The detector 200 generates one or more signals in relation to the detected light beam 211 and send the signals to the controller 300. For example, the detector 200 may be adapted to generate one or more signals in relation to the detected intensities of one or more of a plurality of wavelengths of light diffracted by the periodic pattern 54 of features 52 on the substrate 102. A detector 200 suitable to detect the diffracted light beam and generate the one or more signals may comprise one or more of a diode, a charge-coupled device, and a photomultiplier tube.

Figure 7:
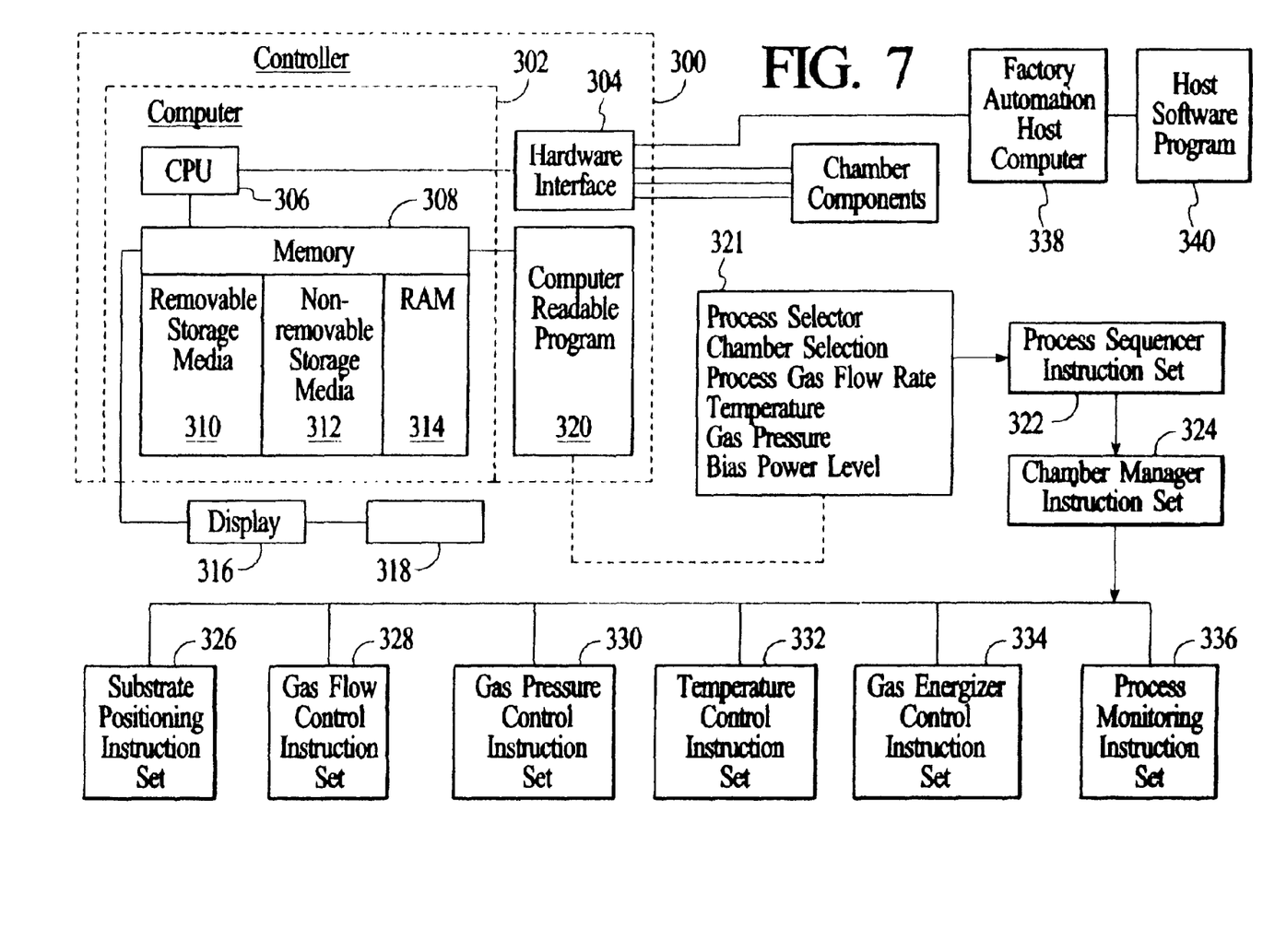
FIG. 7 is an illustrative block diagram of a controller comprising a computer readable program according to an embodiment of the present invention.

The signal from the detector 200 is evaluated by a signal processor, which is a portion of a controller 300, as illustrated in FIG. 7, to monitor the substrate process. The controller 300 and detector 200 may generate the signal trace in discrete intervals or continuously during the processing of the substrate 104. The processes may also be performed in the chamber 106 by operating the chamber components with the controller 300. The controller 300 may comprise a computer 302 having a central processor unit (CPU) 306, such as for example a 68040 microprocessor, commercially available from Synergy Microsystems, California, or a Pentium Processor commercially available from Intel Corporation, Santa Clara, Calif., that is coupled to a hardware interface 304, memory 308 and peripheral computer components, as shown in FIG. 7. Preferably, the memory 308 may include a removable storage medium 310, such as for example a CD or floppy drive, a non-removable storage medium 312, such as for example a hard drive, and random access memory 314. The controller 300 may further comprise a plurality of interface cards including, for example, analog and digital input and output boards, interface boards, and motor controller boards. The interface between an operator and the controller 300 can be, for example, via a display 316 and a light pen 318. The light pen 318 detects light emitted by the monitor display 316 with a light sensor in the tip of the light pen 318. To select a particular screen or function, the operator touches a designated area of a screen on the monitor 316 and pushes the button on the light pen 318. Typically, the area touched changes color, or a new menu is displayed, confirming communication between the user and the controller 300.

The data signals received by and/or evaluated by the controller 300 may be sent to a factory automation host computer 338. The factory automation host computer 338 may comprise a host software program 340 that evaluates data from several systems, platforms or chambers 106, and for batches of substrates 104 or over an extended period of time, to identify statistical process control parameters of (i) the processes conducted on the substrates 104, (ii) a property that may vary in a statistical relationship across a single substrate 104, or (iii) a property that may vary in a statistical relationship across a batch of substrates 104. The host software program 340 may also use the data for ongoing in-situ process evaluations or for the control of other process parameters. A suitable host software program comprises a WORKSTREAM™ software program available from aforementioned Applied Materials. The factory automation host computer 338 may be further adapted to provide instruction signals to (i) remove particular substrates 104 from the processing sequence, for example, if a substrate property is inadequate or does not fall within a statistically determined range of values, or if a process parameter deviates from an acceptable range; (ii) end processing in a particular chamber 106, or (iii) adjust process conditions upon a determination of an unsuitable property of the substrate 104 or process parameter. The factory automation host computer 338 may also provide the instruction signal at the beginning or end of processing of the substrate 104 in response to evaluation of the data by the host software program 340.

In one version the controller 300 comprises a computer readable program 320 may be stored in the memory 308, for example on the non-removable storage medium 312 or on the removable storage medium 310. The computer readable program 320 generally comprises process control software comprising program code to operate the chamber 106 and its components, process monitoring software to monitor the processes being performed in the chamber 106, safety systems software, and other control software, as for example, illustrated in FIG. 7. The computer-readable program 320 may be written in any conventional computer-readable programming language, such as for example, assembly language, C++, Pascal, or Fortran. Suitable program code is entered into a single file, or multiple files, using a conventional text editor and stored or embodied in computer-usable medium of the memory 308. If the entered code text is in a high level language, the code is compiled, and the resultant compiler code is then linked with an object code of pre-compiled library routines. To execute the linked, compiled object code, the user invokes the object code, causing the CPU 306 to read and execute the code to perform the tasks identified in the program.

An illustrative block diagram of a hierarchical control structure of a specific embodiment of a computer readable program 320 according to the present invention is also shown in FIG. 7. Using a light pen interface, a user enters a process set and chamber number into the computer readable program 320 in response to menus or screens displayed on the CRT terminal. The computer readable program includes process selector program code 321 to control the substrate position, gas flow, gas pressure, temperature, RF power levels, and other parameters of a particular process, as well as code to monitor the chamber process. The process sets are predetermined groups of process parameters necessary to carry out specified processes. The process parameters are process conditions, including without limitations, gas composition, gas flow rates, temperature, pressure, and gas energizer settings such as RF or microwave power levels.

The process sequencer instruction set 322 comprises program code to accept a chamber type and set of process parameters from the process selector 321 and to control its operation. The sequencer program 322 initiates execution of the process set by passing the particular process parameters to a chamber manager instruction set 324 that controls multiple processing tasks in the process chamber 106. Typically, the chamber manager instruction set 324 includes a substrate positioning instruction set 326, a gas flow control instruction set 328, a gas pressure control instruction set 330, a temperature control instruction set 332, a gas energizer control instruction set 334, and a process monitoring instruction set 336. Typically, the substrate positioning instruction set 326 comprises program code for controlling chamber components that are used to load the substrate 104 onto the support 110 and optionally, to lift the substrate 104 to a desired height in the chamber 106. The gas flow control instruction set 328 comprises program code for controlling the flow rates of different constituents of the process gas. The gas flow control instruction set 328 regulates the opening size of the gas flow control valves 134 to obtain the desired gas flow rate into the chamber 106. The gas pressure control instruction set 330 comprises program code for controlling the pressure in the chamber 106 by regulating open/close position of the throttle valve 150. The temperature control instruction set 332 comprises program code to control temperatures in the chamber 106, such as for example the temperature of a wall in the chamber 106 or the temperature of the substrate 104. The gas energizer control instruction set 334 comprises program code for setting, for example, the RF power level applied to the antenna 156 by the antenna power supply 155.

The process monitoring instruction set 336 may comprise program code for monitoring a process in the chamber 106, such as an etching or deposition process, and evaluating or processing the signal from a detector to determine a process endpoint. The process monitoring instruction set 336 may also comprise program code to control components of the process monitoring system, such as the light beam source 204 and detector 200. For example, the process monitoring instruction set 336 may comprise program code to control the wavelengths of light generated by the light beam source 204 or may control focusing or collimating of the light beam with the collimator 205. The process monitoring instruction set 336 may also comprise program code to filter the wavelengths of the light beam detected by the detector 200 or the type of signal generated by the detector 200. The process monitoring instruction set 336 may also comprise program code to evaluate the signal generated by the detector 200, for example to provide a signal trace of the intensities of the diffracted light beam as a function of wavelength and to identify a characteristic attribute of the signal trace that is indicative of an endpoint of a substrate processing stage.

The data signals received by and/or evaluated by the controller 300 may also be sent to a factory automation host computer 338. The factory automation host computer 338 may comprise a host software program 340 that evaluates data from several systems, platforms or chambers 106, and for batches of substrates 104 or over an extended period of time, to identify statistical process control parameters of (i) the processes conducted on the substrates 104, (ii) a property that may vary in a statistical relationship across a single substrate 104, or (iii) a property that may vary in a statistical relationship across a batch of substrates 104. The host software program 340 may also use the data for ongoing in-situ process evaluations or for the control of other process parameters. A suitable host software program comprises a WORKSTREAM™ software program available from aforementioned Applied Materials. The factory automation host computer 338 may be further adapted to provide instruction signals to (i) remove particular substrates 104 from the processing sequence, for example, if a substrate property is inadequate or does not fall within a statistically determined range of values, or if a process parameter deviates from an acceptable range; (ii) end processing in a particular chamber 106, or (iii) adjust process conditions upon a determination of an unsuitable property of the substrate 104 or process parameter. The factory automation host computer 338 may also provide the instruction signal at the beginning or end of processing of the substrate 104 in response to evaluation of the data by the host software program 340.

Figure 1C:
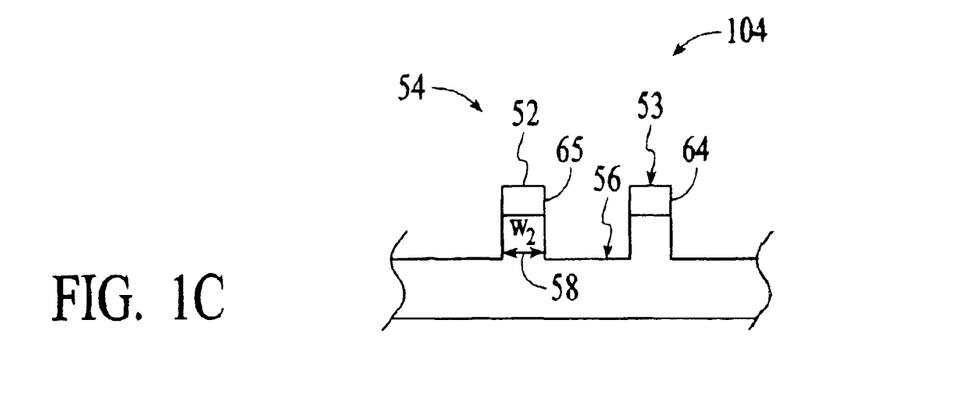

As one example of the present method and apparatus, the endpoint of a mask trimming process that is used to etch and shape a pattern of mask features 52 on the substrate 104 is determined. A mask trimming process is performed to "trim" or etch mask features 52 to desired dimensions, such as a desired width 58. When the mask features are lines, the width is commonly known as a linewidth. During the process, energized etchant gas is provided to etch the edges or sidewalls 64 of the features 52 to decrease the width 58 of the features 52, for example, from a width w1 shown in FIG. 1a to smaller desired width w2 shown in FIG. 1b. A subsequent etching process may be performed to etch the open areas 56 between the features 52 to provide substrate features 52 having the desired width w2, such as those shown in FIG. 1c. Thus, the trimming process generates mask features 52 having smaller critical dimensions, such as smaller width 58, and may be performed, for example, when a critical dimension of a desired feature is too small to be obtained with the conventional lithographic processes.

In one version of a photoresist trimming process, an energized process gas is provided in a chamber 106 to etch features 52 that comprise mask photoresist features 65. A suitable chamber is a DPS 2 chamber for 300 mm to process semiconductor wafers, commercially available from Applied Materials, Inc., Santa Clara, Calif. For example, the energized process gas may include a gas composition capable of etching away the sidewalls of the photoresist features 65 without excessive etching of the features through their vertical thickness. A suitable process gas for etching photoresist features 65 made from carbon based polymeric products, contains oxygen gas which reacts with the carbon based photoresist material to form volatile carbon containing gases such as carbon monoxide and carbon dioxide. It is believed that the $O_2$ serves as the primary etchant for the photoresist, but other gases can also often added, such as for example, HBr to also etch the resist and generate a sidewall protection layer and Ar to generate a more uniform plasma distribution and provide isotropic sputter etching in an inductively coupled plasma environment. A suitable process gas composition includes oxygen, hydrogen bromide, and argon. As an example, the process gas may comprise $O_2$ in a flow rate of from about 5 to about 50 sccm and more typically 25 sccm; HBr in a flow rate of from about 20 to about 200 sccm, and more preferably about 80 sccm; and Ar in a flow rate of from about 0 to about 200 sccm, and more preferably about 20 sccm. The gas pressure in the chamber 106 may be maintained at, for example, from about 1 to about 100 mtorr, and more typically about 4 mtorr. The process gas may be energized by applying a bias power level to the process electrodes of, for example, from about 0 to about 200 Watts, typically about 0 or 20 Watts. A lower bias power level limits loss of the resist in the vertical direction. A source power level applied to the antenna 156 is, for example, from about 200 to about 2000 Watts and mor typically about 600 Watts. The source and bias power levels are typically applied at radio frequencies of from about 50 kHz to about 60 MHz, and often at 13.56 MHz. The rate at which the sidewalls of photoresist features are trimmed is typically from about 0.5 to about 2.5 nm/second. Thus a photoresist feature linewidth of from about 70 nm to about 250 nm may be trimmed to about 70 to about 100 nm. Typically, from about 30 to about 40 nm is trimmed, for example, a linewidth of 130 nm is trimmed down to less than 100 nm.

As the photoresist trimming process is performed, the light beam reflectively diffracted from the substrate 102 by the pattern 54 of photoresist features 65 being etched is monitored. For example, the intensities of a plurality of wavelengths of polarized light diffracted from the substrate 104 is monitored to evaluate the process progress. The endpoint of the process is determined by evaluating the signal trace of the intensities as a function of the plurality of wavelengths and comparing the signal trace to a reference trace to identify a characteristic attribute of the signal trace that is indicative of having attained the predetermined widths w2 of the features 52.

Although exemplary embodiments of the present invention are shown and described, those of ordinary skill in the art may devise other embodiments which incorporate the present invention, and which are also within the scope of the present invention. For example, etching or deposition processes other those specifically described may be performed and monitored according to the present invention, as would be apparent to those of ordinary skill in the art. Also, the process monitoring system may comprise other monitoring components to aid in the monitoring the process, as would be apparent to one of ordinary skill in the art. Furthermore, the terms below, above, bottom, top, up, down, first and second and other relative or positional terms are shown with respect to the exemplary embodiments in the figures and are interchangeable. Therefore, the appended claims should not be limited to the descriptions of the preferred versions, materials, or spatial arrangements described herein to illustrate the invention.

What is claimed is:

1. A substrate processing chamber comprising:
   a support to support a substrate;
   a gas supply to provide a process gas in the chamber;
   a gas energizer to energize the process gas to process the substrate;
   a light beam source comprising one or more lenses adapted to focus and direct a light beam onto a portion of the substrate having a periodic pattern of features while processing the substrate, the light beam comprising multiple wavelengths that are selected so that the light beam is reflectively diffracted by the periodic pattern of features to generate a reflectively diffracted light beam having wavelengths with intensities that modulate if there is a change in the width of the features;
   a light detector to detect the intensities of the multiple wavelengths of the reflectively diffracted light beam and generate a signal in relation to the detected intensities; and
   a controller to receive and evaluate the signal to determine the occurrence of a change in the width of the features from any modulation in the signal.

2. A chamber according to claim 1 wherein the controller is adapted to generate a signal trace from the received signal and compare the generated signal trace to a predetermined reference trace that is representative of the signal trace that is obtained from the diffraction of the light beam from features having a predefined width.

3. A chamber according to claim 2 wherein the controller is adapted to compare the generated signal trace to a predetermined reference trace of an intensify to wavelength $\lambda$ (nm) function that corresponds to $[\sin(\pi b\phi/\lambda)/(\pi b\phi/\lambda)]^2$, where b (nm) is either the width of the features or the width of the open areas between the features, and $\phi$ (radians) is the angle of detection measured from the normal to the surface of the substrate at the substrate location where the light beam is incident.

4. A chamber according to claim 1 wherein the light beam source is a non-pulsed source.

5. A chamber according to claim 1 wherein the light beam source is adapted to generate a light beam having wavelengths of from about 300 to about 700 nm for features having is width of from about 70 to about 250 nm.

6. A chamber according to claim 1 further comprising a light polarizer adapted to polarize the light beam at one or more polarization angles that are selected in relation to a principal orientation of the features.

7. A substrate processing chamber comprising:

a substrate support;

a gas supply to provide a process gas in the chamber;

a gas energizer to energize the process gas to process the substrate;

a light beam source comprising one or more lenses adapted to focus and direct a light beam onto a portion of the substrate having a pattern of features while processing the substrate, the light beam comprising multiple wavelengths that are selected so that the light beam is reflectively diffracted by the periodic pattern of features to generated a reflectively diffracted light beam having wavelengths with intensities that modulate in relation to a width of the features;

a light detector to detect the reflectively diffracted light beam and generate a signal in relation to the intensities of the multiple wavelengths of the reflectively diffracted light beam; and a controller to receive the signal and evaluate the signal to determine the occurrence of a change in the width of the features from a change in the detected intensities of the multiple wavelengths of the reflectively diffracted light beam.

8. A chamber according to claim 7 wherein the controller determines if the features have a predefined width by generating a signal trace from the received signal and comparing the generated signal trace to a predetermined reference trace that is representative of the reflectively diffracted light beam signal when the features have a predefined width.

9. A chamber according to claim 8 wherein the controller is adapted to compare the generated signal trace to a predetermined reference trace of an intensify to wavelength $\lambda$ (nm) function that corresponds to $[\sin(\pi b\phi/\lambda)/(\pi b\phi/\lambda)]^2$, where b (nm) is either the width of the features or the width of the open areas between the features, and $\phi$ (radians) is the angle of detection measured from the normal to the surface of the substrate at the substrate location where the light beam is incident.

* * * * *